(12) United States Patent
Yoon et al.

(10) Patent No.: US 10,149,621 B2
(45) Date of Patent: Dec. 11, 2018

(54) SYSTEM AND METHOD FOR ASSESSING TREATMENT EFFECTS ON OBSTRUCTIVE SLEEP APNEA

(71) Applicant: SEOUL NATIONAL UNIVERSITY BUNDANG HOSPITAL, Gyeonggi-do (KR)

(72) Inventors: In-Young Yoon, Seoul (KR); Kyooseob Ha, Seoul (KR); Jae Seung Chang, Seoul (KR)

(73) Assignee: SEOUL NATIONAL UNIVERSITY BUNDANG HOSPITAL, Gyeonggi-Do (KR)

( * ) Notice: Subject to any disclaimer, the term of this patent is extended or adjusted under 35 U.S.C. 154(b) by 1166 days.

(21) Appl. No.: 14/450,244

(22) Filed: Aug. 3, 2014

(65) Prior Publication Data
US 2015/0223699 A1    Aug. 13, 2015

(30) Foreign Application Priority Data

Feb. 11, 2014   (KR) .................. 10-2014-0015316

(51) Int. Cl.
*A61B 5/0205* (2006.01)
*A61B 5/00* (2006.01)
(Continued)

(52) U.S. Cl.
CPC ........ *A61B 5/0205* (2013.01); *A61B 5/02405* (2013.01); *A61B 5/0816* (2013.01);
(Continued)

(58) Field of Classification Search
None
See application file for complete search history.

(56) References Cited

U.S. PATENT DOCUMENTS

| 6,168,568 B1* | 1/2001 | Gavriely ............... A61B 5/087 |
| | | 600/529 |
| 2003/0045806 A1* | 3/2003 | Brydon ............... A61B 5/0816 |
| | | 600/534 |

(Continued)

FOREIGN PATENT DOCUMENTS

KR    10-2010-0045521 A     5/2010

OTHER PUBLICATIONS

Al-Angari, Haitham M., and Alan V. Sahakian. "Use of sample entropy approach to study heart rate variability in obstructive sleep apnea syndrome." IEEE Transactions on Biomedical Engineering 54.10 (2007): 1900-1904.*

(Continued)

*Primary Examiner* — Patricia Mallari
*Assistant Examiner* — Jairo Portillo
(74) *Attorney, Agent, or Firm* — The PL Law Group, PLLC

(57) ABSTRACT

A system and method for assessing treatment effects on obstructive sleep apnea are provided. The apparatus includes a bio-signal measurement unit, a combined index calculation unit, and a treatment response assessment unit. The bio-signal measurement unit measures each of the electrocardiogram and respiratory rhythm of a patient. The combined index calculation unit calculates a combined cardiac and respiratory index by combining the heart rate variability and respiratory rhythm signals measured by the bio-signal measurement unit. The treatment response assessment unit assesses a response of the patient to the treatment of obstructive sleep apnea.

7 Claims, 11 Drawing Sheets

(51) Int. Cl.
*A61M 16/04* (2006.01)
*A61B 5/024* (2006.01)
*A61B 5/08* (2006.01)
*A61M 16/14* (2006.01)
*A61M 16/00* (2006.01)

(52) U.S. Cl.
CPC .......... *A61B 5/4818* (2013.01); *A61B 5/4848* (2013.01); *A61M 16/04* (2013.01); *A61M 16/0488* (2013.01); *A61M 16/14* (2013.01); *A61M 2016/0033* (2013.01); *A61M 2202/0208* (2013.01); *A61M 2202/0468* (2013.01); *A61M 2205/581* (2013.01); *A61M 2205/584* (2013.01); *A61M 2205/8206* (2013.01)

(56) References Cited

U.S. PATENT DOCUMENTS

| | | | |
|---|---|---|---|
| 2007/0032733 A1* | 2/2007 | Burton | A61B 5/02405 600/509 |
| 2008/0004904 A1* | 1/2008 | Tran | A61B 5/0006 705/2 |
| 2009/0076405 A1* | 3/2009 | Amurthur | A61B 5/0002 600/529 |
| 2010/0217133 A1* | 8/2010 | Nilsen | A61B 5/0205 600/484 |
| 2011/0066043 A1* | 3/2011 | Banet | A61B 5/022 600/485 |
| 2012/0156933 A1* | 6/2012 | Kreger | A61B 5/02433 439/625 |
| 2014/0276174 A1* | 9/2014 | Hyde | A61M 16/0051 600/534 |

OTHER PUBLICATIONS

Richman, Joshua S., and J. Randall Moorman. "Physiological time-series analysis using approximate entropy and sample entropy." American Journal of Physiology-Heart and Circulatory Physiology 278.6 (2000): H2039-H2049.*

Shi, Wenbin, and Pengjian Shang. "Cross-sample entropy statistic as a measure of synchronism and cross-correlation of stock markets." Nonlinear Dynamics 71.3 (2013): 539-554.*

Yasuma, Fumihiko, and Jun-ichiro Hayano. "Respiratory sinus arrhythmia: why does the heartbeat synchronize with respiratory rhythm?." Chest Journal 125.2 (2004): 683-690.*

Chang et al., Enhanced cardiorespiratory coupling in patients with obstructive sleep apnea following continuous positive airway pressure treatment, Sleep Med. Nov. 2013;14(11):1132-8.

* cited by examiner

SYSTEM AND METHOD FOR ASSESSING TREATMENT EFFECTS ON OBSTRUCTIVE SLEEP APNEA

CROSS-REFERENCE TO RELATED APPLICATION

This application claims priority to and the benefit of Korean Patent Application No. 10-2014-0015316, filed Feb. 11, 2014, the disclosure of which is incorporated herein by reference in its entirety.

BACKGROUND

1. Technical Field

The present disclosure relates to a system and method for assessing treatment effects on obstructive sleep apnea, which are capable of objectively quantifying a response to the treatment of obstructive sleep apnea, providing a cardiac and respiratory index that can be used for clinical assessment, and assessing the effects of the treatment based on the respiratory index.

2. Description of the Related Art

In general, obstructive sleep apnea (OSA) is a disorder that is associated with sleep disordered breathing and that repeatedly obstructs a portion of the upper airway or the entire upper airway during sleep, thus resulting in nocturnal hypoxia and daytime sleepiness. Chronic hypoxia leads to inflammatory cytokines, the dysfunction of the sympathetic nervous system, endothelial dysfunction, and an increase in death caused by cardiovascular disease. Although the association of OSA with a change in the cardiovascular system in a biological mechanism is unclear, it was reported that an abnormality in central autonomic regulation leads to an increase in the risk of development of cardiovascular disease in OSA patients. In OSA research, heart rate variability (HRV) is frequently used for regulation of autonomic nerves and is based on changes in the R-R intervals of digital electrocardiograms (ECGs), as disclosed in Korean Patent Application Publication No. 10-2010-0045521 (published on May 3, 2010). Previous research indicates that a decrease in the heart rate variability (HRV) of an OSA patient leads to abnormal autonomic regulation and an increase in the risk of a cardiovascular event.

Meanwhile, it is known that continuous positive airway pressure (CPAP) is standard treatment for OSA, and can provide beneficial effects on the HRV index of OSA patients. However, the effects of CPAP on the combined cardiac and respiratory index remain unclear, and there is currently no index that can be used to quantitatively objectify the response of a patient to CPAP standard treatment and the effects of CPAP standard treatment.

SUMMARY

At least one embodiment of the present invention is intended to provide a system for assessing treatment effects on obstructive sleep apnea, which is capable of measuring heart rate variability and respiratory rhythm signals at the same time, calculating a combined cardiac and respiratory index, and then assessing a response to the treatment of obstructive sleep apnea based on the combined cardiac and respiratory index.

At least one embodiment of the present invention is intended to provide a system for assessing treatment effects on obstructive sleep apnea, which includes a combined index calculation unit, thereby calculating a combined cardiac and respiratory index that can be used to assess the coordination between heart rate and respiratory rhythm.

At least one embodiment of the present invention is intended to provide a system or method for assessing treatment effects on obstructive sleep apnea, which are capable of assessing treatment effects on obstructive sleep apnea based on quantified values, such as a change in the calculated combined cardiac and respiratory index or a difference of the calculated combined cardiac and respiratory index from that of a normal control.

At least one embodiment of the present invention is intended to provide a system for assessing treatment effects on obstructive sleep apnea, which further includes a customized management unit, thereby establishing a treatment method and a plan for each patient based on treatment effects on obstructive sleep apnea.

At least one embodiment of the present invention is intended to provide a system for assessing treatment effects on obstructive sleep apnea, which further includes a treatment/assessment information unit, thereby storing and managing information about the combined cardiac and respiratory index of a normal control and information about the history of the treatment of obstructive sleep apnea of a patient.

At least one embodiment of the present invention is intended to provide a system for assessing treatment effects on obstructive sleep apnea, in which a bio-signal measurement unit has been implemented in the form of a portable unit, thereby enabling information about the heart rate variability and respiratory rhythm of a patient to be measured at a remote location and transmitted in real time.

At least one embodiment of the present invention is intended to provide a method of assessing treatment effects on obstructive sleep apnea, which is capable of comparing a combined cardiac and respiratory index, obtained by combining the heart rate variability and respiratory rhythm signals of the patient, with those of a normal control, thereby assessing the response of a patient to standard treatment for obstructive sleep apnea.

In accordance with an aspect of the present disclosure, there is provided a system for assessing treatment effects on obstructive sleep apnea, the system including a bio-signal measurement unit configured to measure each of the electrocardiogram and respiratory rhythm of a patient; a combined index calculation unit configured to calculate a combined cardiac and respiratory index by combining the heart rate variability and respiratory rhythm signals measured by the bio-signal measurement unit; and a treatment response assessment unit configured to assess a response of the patient to the treatment of obstructive sleep apnea.

The combined index calculation unit may include a heart rate variability entropy calculation unit configured to calculate a non-linear sample entropy index that is used to assess time series regularity of heart rate variability; a respiratory rhythm entropy calculation unit configured to calculate a non-linear sample entropy index that is used to assess time series regularity of respiratory rhythm; and a cross-sample entropy calculation unit configured to calculate the combined cardiac and respiratory index by combining a heart rate variability entropy index with a respiratory rhythm entropy index.

The treatment response assessment unit may be configured to assess the treatment effects on obstructive sleep apnea based on a change in the combined cardiac and respiratory index or a difference of the combined cardiac and respiratory index from that of a normal control, and may be also configured to determine that the coordination between heart rate and respiratory rhythm is low if a value of the combined cardiac and respiratory index is higher than an upper limit of a normal range, and determine that the coordination between heart rate and respiratory rhythm is high if the value of the combined cardiac and respiratory index is lower than a lower limit of the normal range.

The system may further include a customized management unit connected with the treatment response assessment unit, and configured to establish a treatment method and a plan for the patient based on treatment effects on obstructive sleep apnea.

The system may further include a treatment/assessment information unit connected with the treatment response assessment unit, and configured to store and manage information about the combined cardiac and respiratory index of a normal control and information about a history of treatment of obstructive sleep apnea of the patient.

The bio-signal measurement unit may be implemented in a portable form that can be carried by the patient, and may be attached to or worn on a wrist and chest of the patient and measure the electrocardiogram and respiratory rhythm of the patient; and may further include a separate data communication unit, and may transmit the measured electrocardiogram and respiratory rhythm to an external location.

In accordance with an aspect of the present disclosure, there is provided a method of assessing treatment effects on obstructive sleep apnea, the method including step (a) measuring each of an electrocardiogram and respiratory rhythm of a patient using a bio-signal measurement unit; step (b) calculating a combined cardiac and respiratory index by combining the heart rate variability and respiratory rhythm signals, measured at step (a), using a combined index calculation unit; step (c) comparing the calculated combined cardiac and respiratory index with that of a normal control group using a treatment response assessment unit; and step (d) assessing a level of post-treatment recovery on based on results of the comparison.

Step (b) may include step (b-1) calculating heart rate sample entropy ($SampEn_{RR}$) and respiratory rhythm sample entropy ($SampEn_{rep}$) using a heart rate entropy calculation unit and a respiratory rhythm entropy calculation unit, respectively; and step (b-2) calculating the combined cardiac and respiratory index (Cross-SampEn) by combining the heart rate sample entropy with the respiratory rhythm sample entropy using a cross-sample entropy calculation unit.

BRIEF DESCRIPTION OF THE DRAWINGS

The above and other objects, features and advantages of the present disclosure will be more clearly understood from the following detailed description taken in conjunction with the accompanying drawings, in which.

DETAILED DESCRIPTION

A system and method for assessing treatment effects on obstructive sleep apnea according to embodiments of the present disclosure will be described in detail below.

Figure 1:
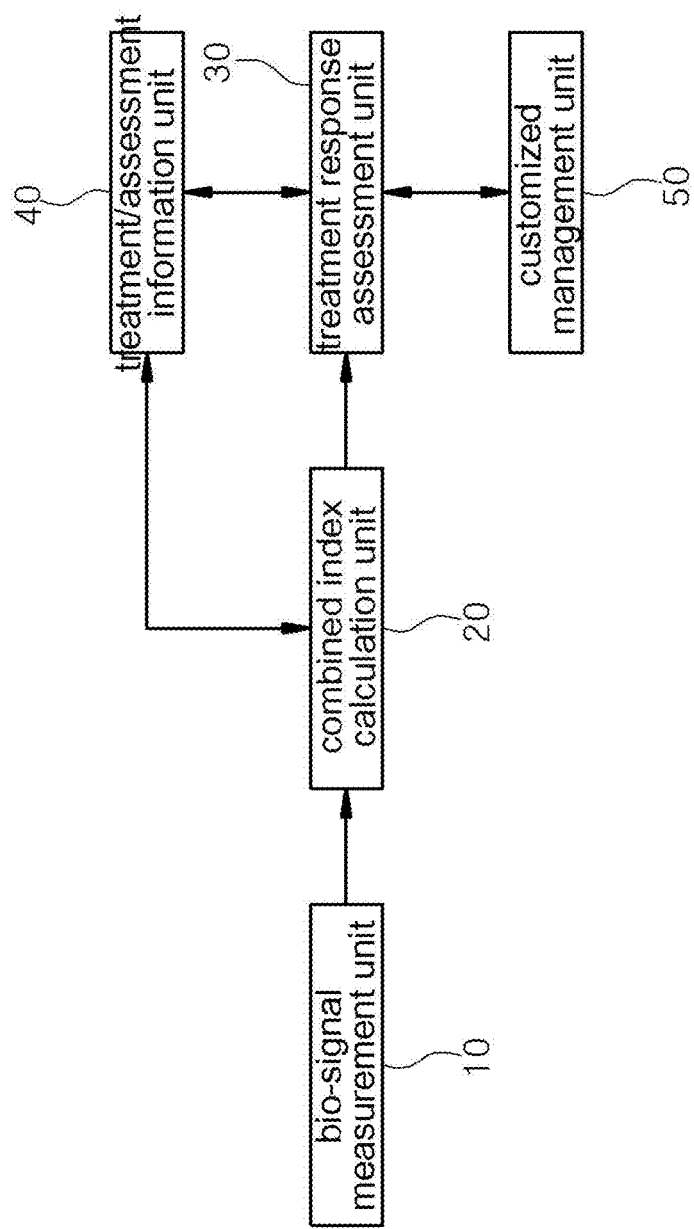
FIG. 1 is a diagram illustrating the overall configuration of a system for assessing treatment effects on obstructive sleep apnea according to an embodiment of the present disclosure.

FIG. 1 is a diagram illustrating the overall configuration of a system for assessing treatment effects on obstructive sleep apnea according to an embodiment of the present disclosure. Referring to FIG. 1, the system includes a bio-signal measurement unit 10, a combined index calculation unit 20, a treatment response assessment unit 30, a treatment/assessment information unit 40, and a customized management unit 50.

Figure 2:
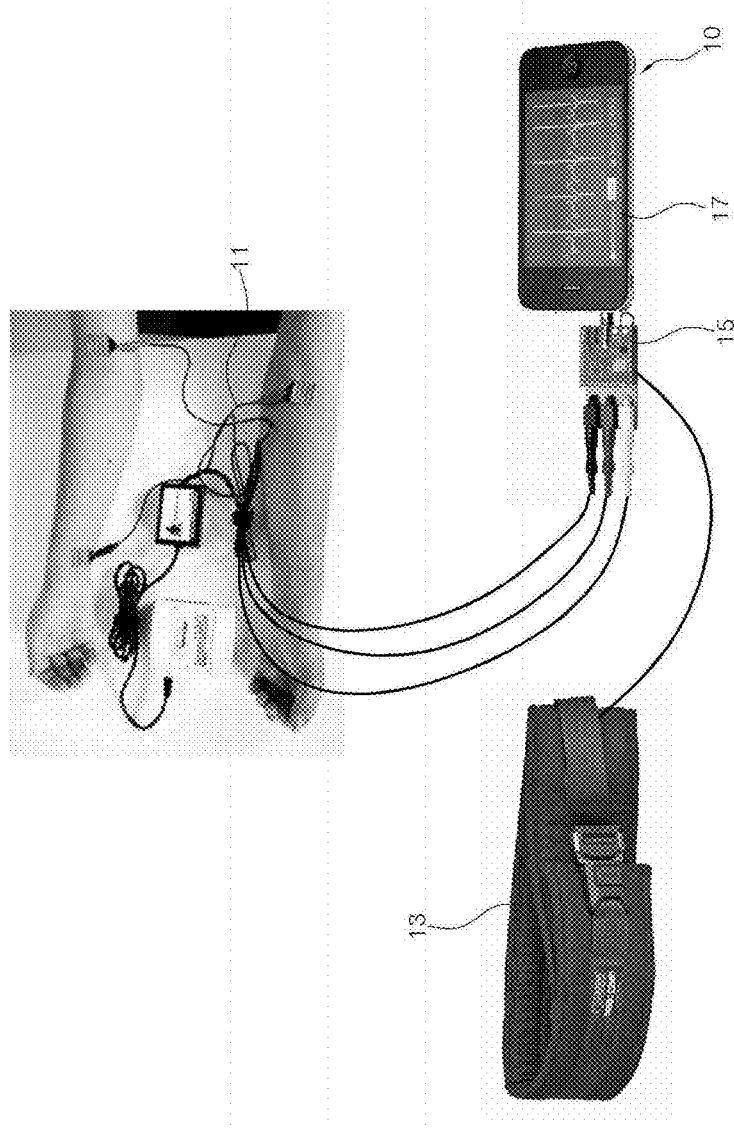
FIG. 2 is a view illustrating an embodiment of the bio-signal measurement unit of the system for assessing treatment effects on obstructive sleep apnea according to an embodiment of the present disclosure.

The bio-signal measurement unit 10 measures each of the electrocardiogram and respiratory rhythm of a patient. A conventional examination device that is used in hospitals may be used as the bio-signal measurement unit 10. As illustrated in FIG. 2, the bio-signal measurement unit 10 may be implemented in the form of a portable unit.

The bio-signal measurement unit 10 that is implemented in the form of a portable device includes an electrocardiogram measurement unit 11, a respiratory rhythm measurement unit 13, a measured signal control unit 15, and a data communication unit 17. In an embodiment, the data communication unit 17 may be implemented as a mobile communication terminal, such as a smartphone.

Using this bio-signal measurement unit 10, a patient may measure his or her bio-signal at home by attaching the electrocardiogram measurement unit 11 to both arms and also wearing the respiratory rhythm measurement unit 13 on the chest. The measured bio-signal may be transferred to the measured signal control unit 15, and may be transmitted via the data communication unit 17 to an external hospital server.

When the bio-signal measurement unit 10 is implemented in the form of a portable unit as described above, the condition of the patient may be monitored in real time, and treatment effects on the obstructive sleep apnea of the patient may be easily assessed.

Figure 3:
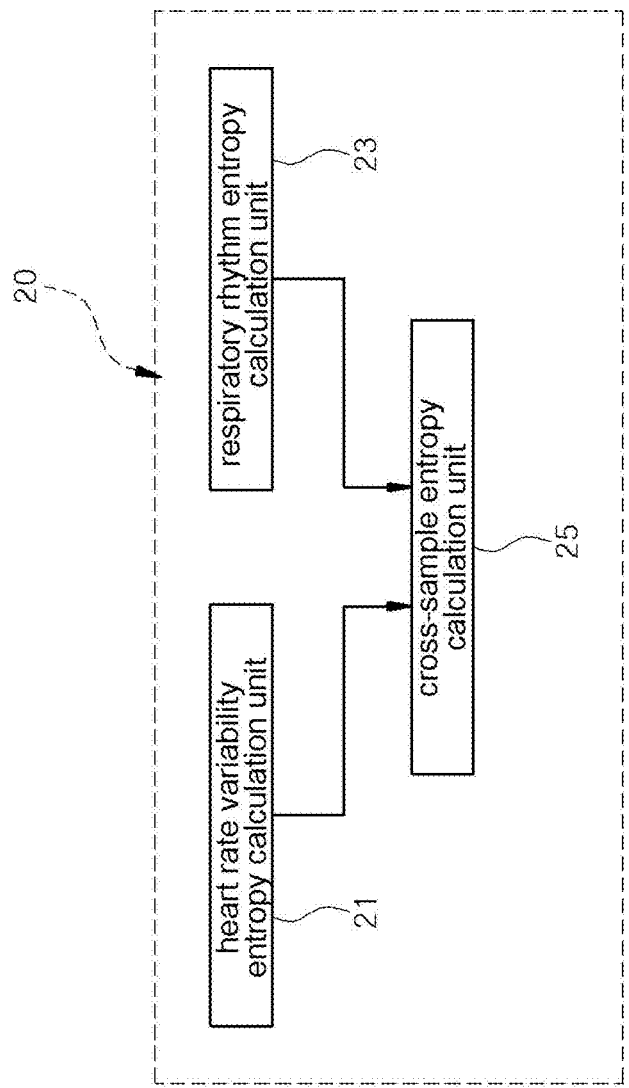
FIG. 3 is a diagram illustrating the detailed configuration of the combined index calculation unit of the system for assessing treatment effects on obstructive sleep apnea according to an embodiment of the present disclosure.

The combined index calculation unit 20 calculates a combined cardiac and respiratory index by combining the electrocardiogram and respiratory rhythm signals measured by the bio-signal measurement unit. As illustrated in FIG. 3, the combined index calculation unit 20 includes a heart rate variability entropy calculation unit 21, a respiratory rhythm calculation unit 23, and a cross sample entropy calculation unit 25.

The heart rate variability entropy calculation unit 21 calculates a non-linear sample entropy index $SampEn_{RR}$ used to assess the time series regularity and complexity of heart rate variability, and the respiratory rhythm calculation unit 23 calculates a non-linear sample entropy index $SampEn_{rep}$ used to assess the time series regularity and complexity of respiratory rhythms.

SampEn may be applied to short time series data, excluding self-matching. While SampEn is similar to conventional approximative entropy ApEn, it may overcome the disadvantage of the conventional approximative entropy.

In an embodiment of the present disclosure, the heart rate variability sample entropy and the respiratory rhythm sample entropy are defined as follows:

For example, given a time series of $x(i)=1, 2, 3, \ldots, N$, input parameters m and r can be selected, where m is the size of the regeneration vector of a phase and r is a filtering level. When m samples begin at sample $x(i)$, vector $v_m(i)$ is expressed as $[x(i), x(i+1), \ldots, x(i+m-1)]$, and all vector sets having length m, such as $[v_m(1), v_m(2), \ldots, v_m(N-m)]$ within $x(n)$, are taken into account. The density correlation function $C_{i,m}(r)$ is defined as the following Equation 1

$$C_{i,m}(r) = \frac{n_{i,m}(r)}{N-m+1} \quad (1)$$

where $n_{i,m}(r)$ is the number of vectors similar to $v_m(i)$, the pseudo-criterion r is given, and self-matching is excluded. For i, a similar calculation is made in each of $i=1, 2, \ldots, N-m$. The function $C_m(r)$ is the average of $C_{i,m}(r)$, and is defined as the following Equation 2

$$C_m(r) = \frac{\sum_{i=1}^{N-m} C_{i,m}(r)}{N-m} \quad (2)$$

Similarly, $C_{i,(m+1)}(r)$ is defined as the following Equation 3:

$$C_{i,(m+1)}(r) = \frac{n_{i(m+1)}(r)}{N-m-1} \quad (3)$$

where $n_{i,(m+1)}(r)$ is the number of vectors in a sequence of $[v_{m+1}(1), v_{m+1}(2), \ldots, v_{m+1}(N-m)]$ and is similar to $v_{m+1}(i)$, the pseudo-criterion r is given, and self-matching is excluded. For i, a similar calculation is made in each of $i=1, 2, \ldots, N-m$. The function $C_{(m+1)}(r)$ is the average of $C_{i,(m+1)}(r)$, and is defined as the following Equation 4:

$$SampEn(m,r,N) = -\ln(C_{m+1}(r)/C_m(r)) \quad (4)$$

These equations represent the negative natural logarithm of the conditional probability. These equations indicate that, when self-matching is not included, two similar sequences at point m are still similar at the next point. In an embodiment of the present disclosure, open-source software available from PhysioNet was used for the calculation of SampEn, the analysis of HRV and the calculation of SampEn were performed using a Matlab software package, and signals were processed using Toolbox.

Figure 4:
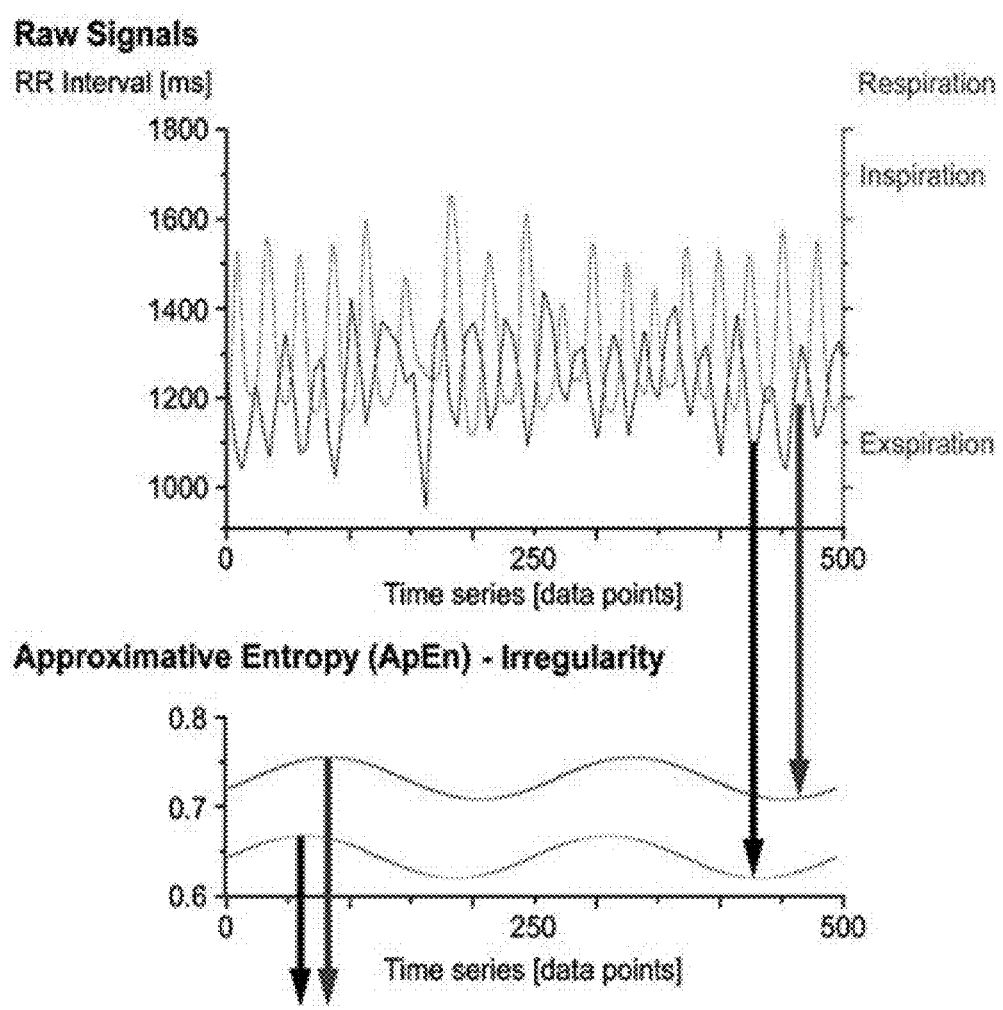
FIG. 4 is graphs illustrating the concept of calculating a combined cardiac and respiratory index that is used in the system for assessing treatment effects on obstructive sleep apnea according to an embodiment of the present disclosure.

As illustrated in FIG. 4, the cross-sample entropy calculation unit 25 combines the heart rate variability entropy index $SampEn_{RR}$ with the respiratory rhythm entropy index $SampEn_{rep}$, and then calculates a combined cardiac and respiratory index Cross-SampEn.

Figure 5:
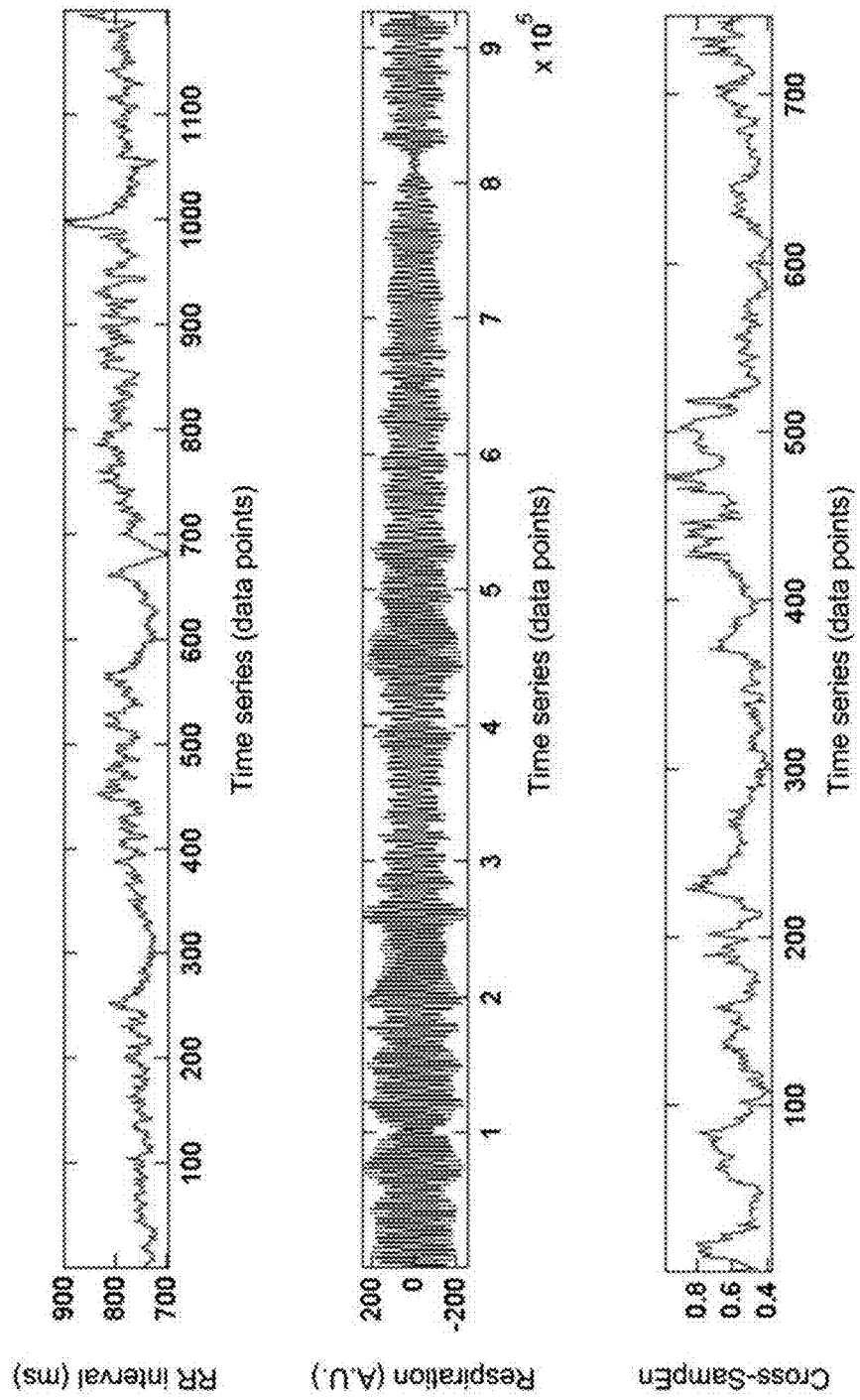
FIG. 5 is a graph illustrating the RR interval, respiration and Cross-SampEn against time series.
Figure 6A:
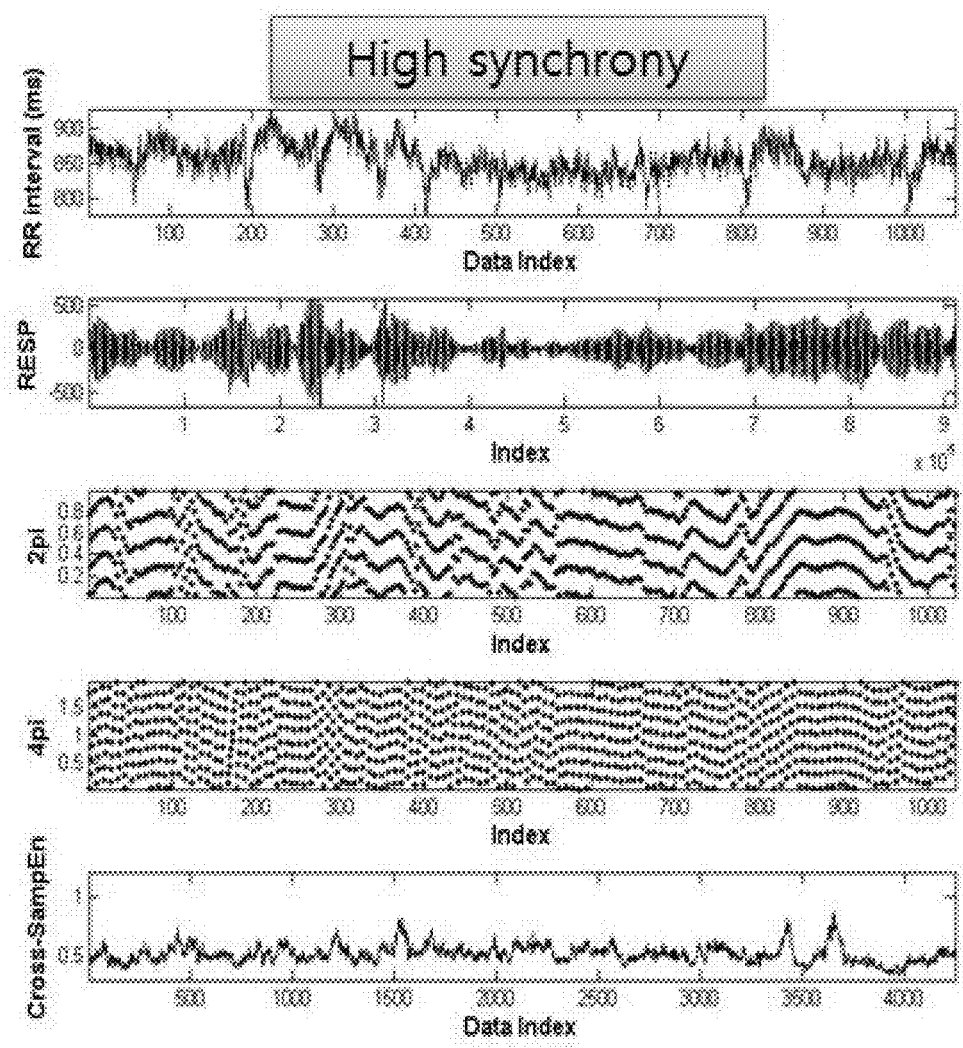
FIGS. 6A and 6B are graphs illustrating coordination based on combined cardiac and respiratory indices in the system for assessing treatment effects on obstructive sleep apnea according to an embodiment of the present disclosure.
Figure 6B:
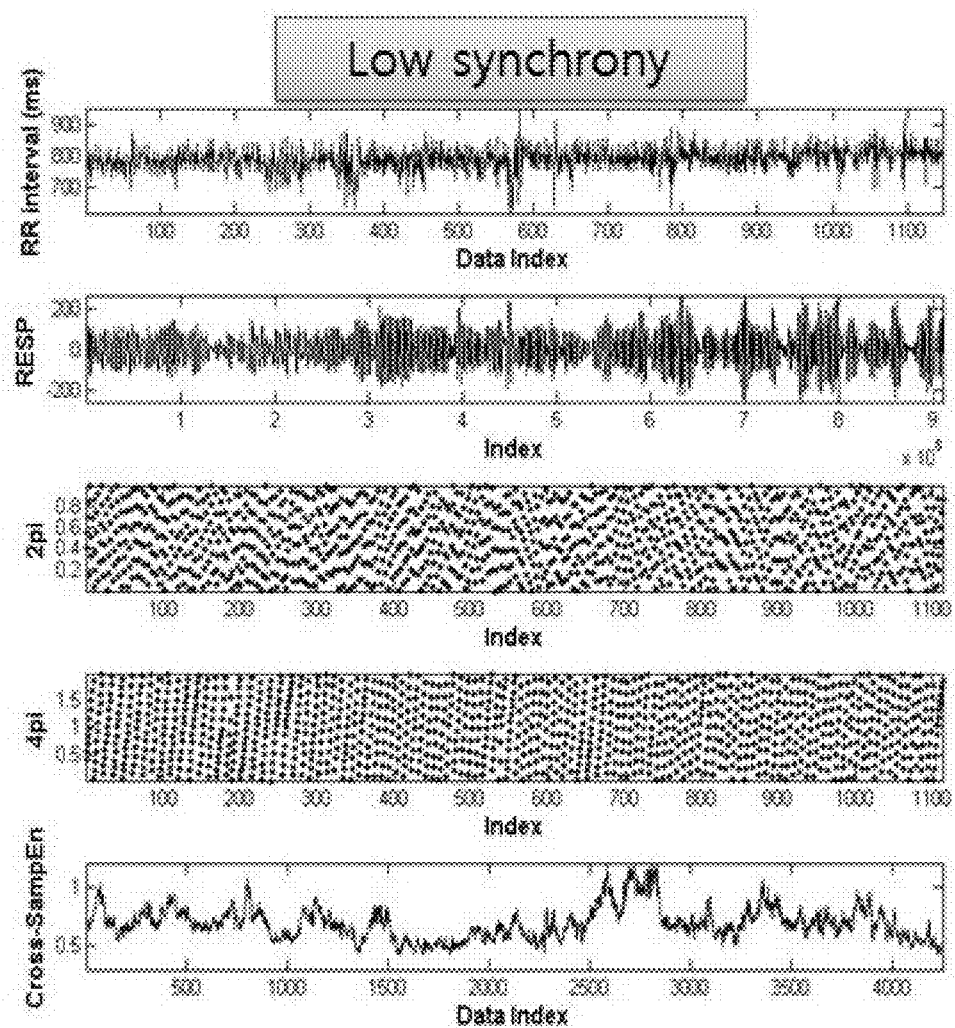

In an embodiment of the present disclosure, Cross-SampEn values are used to quantify the reaction between time series (i.e., the heart rate and the respiration) that are separate but interact with each other under the influence of a central autonomic network. FIG. 5 illustrates the time series of raw signals (RR intervals and respiratory intervals), and also illustrates the Cross-SampEn values of a representative control. The normal range of the combined cardiac and respiratory index Cross-SampEn may be a range from 0.46 to 0.58. Re-sampling at 5 Hz is used to generate a number of respiratory intervals equal to the number of RR intervals. As illustrated in FIG. 6A, when the coordination between the RR intervals and the respiratory intervals is strong, the Cross-SampEn value is low and the cardiorespiratory coupling (CRC) level is high. However, as illustrated in FIG. 6B, when the coordination between two time series data sets is weak, the Cross-SampEn value is high, and is associated with low synchrony.

The treatment response assessment unit 30 accesses the treatment response of the patient based on the combined cardiac and respiratory index calculated by the combined index calculation unit 20, and grades the effect of standard treatment CPAP (continuous positive airway pressure) on obstructive sleep apnea based on a change in the combined cardiac and respiratory index or a difference from that of a normal control. Furthermore, if the value of the combined cardiac and respiratory index is higher than the upper limit of the normal range, the treatment response assessment unit 30 determines that the coordination between heart rate variability and respiratory rhythm is low and then takes into account the level of an abnormality in central autonomic regulation. In contrast, if the value of the combined cardiac and respiratory index is lower than the lower limit of the normal range, the treatment response assessment unit 30 determines that the coordination between heart rate variability and respiratory rhythm is high.

The system for assessing treatment effects on obstructive sleep apnea according to the embodiment of the present disclosure may further include the treatment/assessment information unit 40, and the customized management unit 50.

The treatment/assessment information unit 40 is connected with the treatment response assessment unit 30, and stores and manages information about the combined cardiac and respiratory index of a normal control and information about the history of the treatment of the obstructive sleep apnea of the patient. Accordingly, using the treatment/assessment information unit 40, information about the combined cardiac and respiratory index of a normal control and information about the history of the treatment of the obstructive sleep apnea of the patient can be systematically managed, and the objectivity and accuracy of the assessment of the treatment response of the patient can be ensured.

In addition, the customized manage unit 50 is connected with the treatment response assessment unit 30, and establishes a treatment method and a plan for each patient based on the effects of standard treatment on obstructive sleep apnea. Using the customized manage unit 50, patient-customized treatment is enabled, and thus the treatment period of obstructive sleep apnea can be reduced and also treatment effects on obstructive sleep apnea can be enhanced.

As described above, when the system for assessing treatment effects on obstructive sleep apnea is applied, a combined cardiac and respiratory index is calculated by measuring electrocardiograph and respiratory rhythm signals at the same time, and thus an abnormality in central autonomic regulation can be objectively quantified and also the onset of a cardiovascular disease can be predicted and prevented in advance.

In addition, since the system can check the condition of the patient in a non-invasive manner, it does not cause discomfort to the patient, and can minimize the repulsion of the patient toward the examination of treatment response.

A method of assessing treatment effects using the system for assessing treatment effects on obstructive sleep apnea according to an embodiment of the present disclosure will be described below.

Figure 7:
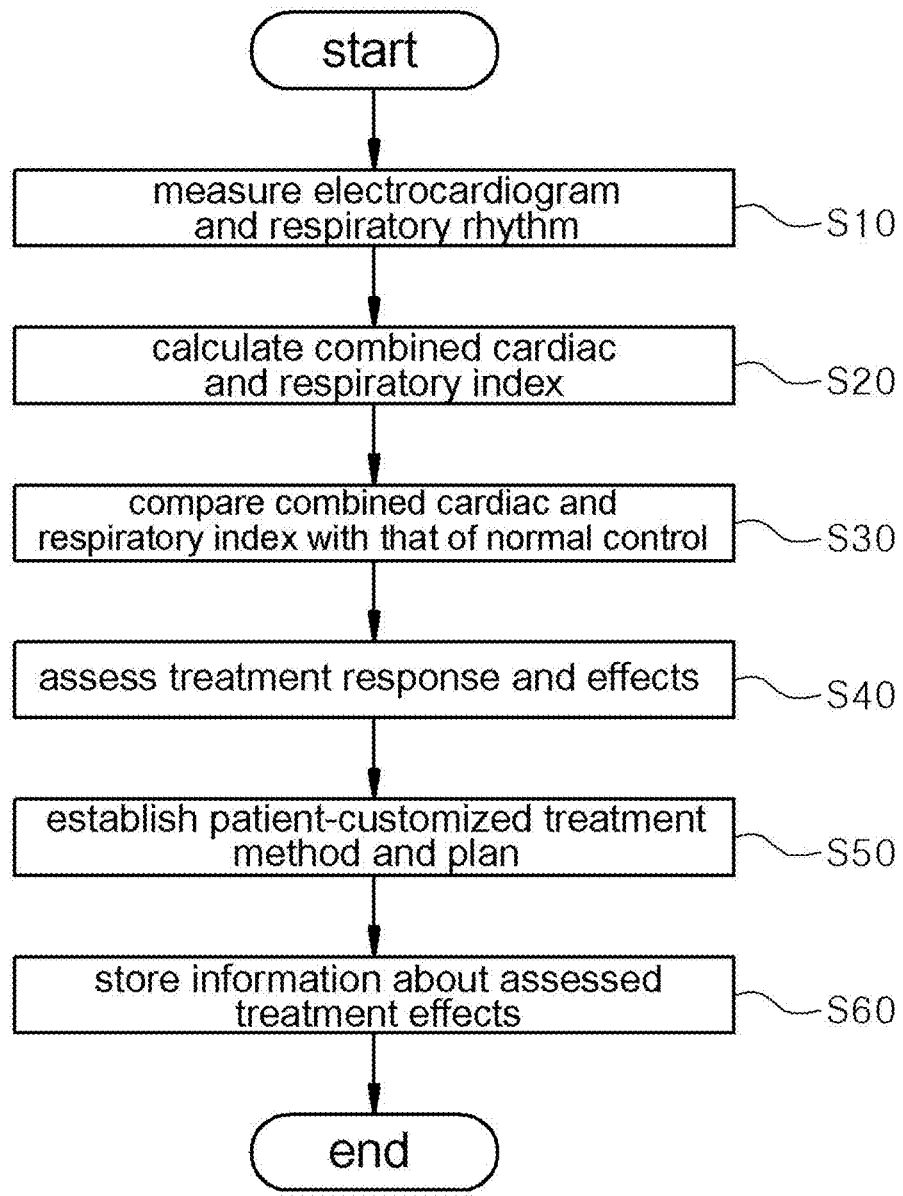
FIG. 7 is a flowchart illustrating a method of assessing treatment effects on obstructive sleep apnea according to an embodiment of the present disclosure.

FIG. 7 is a flowchart illustrating the method of assessing treatment effects on obstructive sleep apnea according to this embodiment of the present disclosure. Referring to FIG. 7, step S10 of measuring each of the electrocardiogram and respiratory rhythm of a patient using the bio-signal measurement unit 10 is performed.

Figure 8:
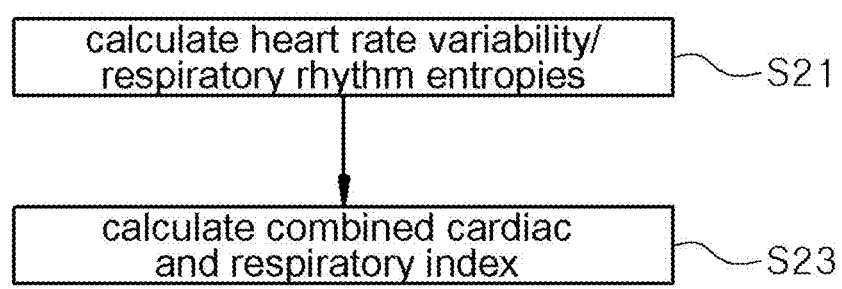
FIG. 8 is a detailed flowchart illustrating step S20 of the method of assessing treatment effects on obstructive sleep apnea according to an embodiment of the present disclosure.

Thereafter, step S20 of calculating a combined cardiac and respiratory index by combining the heart rate variability and respiratory rhythm, measured at step S10, using the combined index calculation unit 20, is performed. As illustrated in detail in FIG. 8, step S20 includes step S21 of calculating heart rate variability sample entropy $SampEn_{RR}$ and respiratory rhythm sample entropy $SampEn_{rep}$ using the heart rate variability entropy calculation unit 21 and the respiratory rhythm entropy calculation unit 23. The heart rate variability/respiratory rhythm sample entropies in the present disclosure are as defined in the above Equation 4. Step S21 is followed by step S23 of calculating a combined cardiac and respiratory index (Cross-SampEn) by combining the heart rate variability sample entropy with the respiratory rhythm sample entropy using the cross-sample entropy calculation unit 25.

Thereafter, step S30 of comparing the calculated combined cardiac and respiratory index with that of a normal control using the treatment response assessment unit 30. Step S40 of assessing the level of post-treatment recovery is performed based on the results of the comparison.

At step S40, treatment response is assessed based on a change in the combined cardiac and respiratory index and a difference from the normal control. In this case, if the value of the combined cardiac and respiratory index is higher than the upper limit of the normal range, it is determined that the coordination between heart rate variability and respiratory rhythm is low, and the level of an abnormality in central autonomic regulation is taken into account. In contrast, if the value of the combined cardiac and respiratory index is lower than the lower limit of the normal range, it is determined that the coordination between heart rate variability and respiratory rhythm is high.

Thereafter, step S50 of establishing a treatment method and a plan for the patient based on the effects of standard treatment on obstructive sleep apnea using the customized management unit 50 is performed. Thereafter, step S60 of storing information about the combined cardiac and respiratory index of a normal control and information about information about the history of the treatment of the obstructive sleep apnea of the patient using the treatment/assessment information unit 40 is performed.

The system, method, components and units described in conjunction with FIGS. 1 to 8 may be implemented in the form of a computer-readable storage medium including computer-executable instructions, such as one or more computer-executable applications or modules.

The computer-readable storage medium may be any available medium that can be accessed by a computer, and includes volatile and nonvolatile media and removable and non-removable media.

Additionally, the computer-readable storage medium may include both a computer storage medium and a communication medium. The computer-readable storage medium may include volatile and nonvolatile media and removable and non-removable media that are implemented using any method or technology for storing information, such as computer-readable instructions, a data structure, a module or other types of data.

The term "module" may refer to hardware capable of performing a function and operation based on the name of each component described herein, computer program code capable of performing a specific function and operation, or an electronic storage medium on which computer program code capable of performing a specific function and operation has been installed.

Through the following test, the effects of the method of assessing treatment effects on obstructive sleep apnea according to an embodiment of the present disclosure can be assessed.

13 middle-aged men suffering from obstructive sleep apnea (OSA) and 13 healthy middle-aged men functioning as a normal control group participated in this test. The following Table 1 shows the demographic characteristics and polysomnographic characteristics of the two groups.

TABLE 1

Clinical and demographic characteristics of the study sample.

| | Control group | OSA group (n = 13) | |
|---|---|---|---|
| | (n = 13) | Pre-CPAP | Post-CPAP |
| Age, mean (SD), y | 46.0 (9.4) | 49.8 (7.0) | |
| Education, mean (SD), y | 16.1 (2.7) | 15.1 (3.0) | |
| MMSE score, mean (SD) | 29.3 (0.8) | 29.3 (1.2) | |
| BMI, mean| (SD), kg/m[2a] | 23.7 (1.9) | 30.6 (4.6) | 30.1 (4.4) |
| AHI, mean (SD), n/h[a,b] | 4.1 (3.7) | 60.3 (21.2) | 3.8 (2.2) |
| ODI, mean (SD), n/h[a] | 1.6 (1.3) | 54.6 (23.0) | — |
| Time with SpO$_2$ < 90%[a] | 0.01 (0.02) | 22.8 (24.4) | — |
| Inspiration, mean (SD), ms | 1521.9 (197.6) | 1520.9 (151.5) | 1531.5 (99.7) |
| Expiration, mean (SD), ms | 2243.3 (243.7) | 2219.6 (164.7) | 2201.5 (127.4) |
| Duty cycle, mean (SD), % | 40.9 (5.7) | 40.7 (3.8) | 41.0 (2.8) |
| PSQI score, mean (SD)[b] | 5.8 (2.1) | 6.4 (3.1) | 3.7 (1.8) |
| ESS score, mean (SD)[b] | 9.8 (5.4) | 12.3 (5.7) | 6.7 (5.3) |
| BDI score, mean (SD)[b] | 3.2 (3.6) | 6.7 (5.5) | 3.7 (2.8) |

TABLE 1-continued

Clinical and demographic characteristics of the study sample.

| | Control group (n = 13) | OSA group (n = 13) | |
|---|---|---|---|
| | | Pre-CPAP | Post-CPAP |
| CPAP pressure, mean (SD), mm H$_2$O | — | 11.2 (2.1) | |
| CPAP duration, mean (SD), d | — | 93.8 (19.8) | |
| CPAP compliance, mean (SD), % | — | 78.9 (14.5) | |

Abbreviations: OSA, obstructive sleep apnea; CPAP, continuous positive airway pressure; SD, standard deviation; y, years; MMSE, Mini-Mental State Examination (a measure of general cognition); BMI, body mass index; AHI, apnea-hypopnea index; n/h, number per hour; ODI, oxygen desaturation index; SpO$_2$, oxygen saturation; Duty cycle, percent inspiratory time; PSQI, Pittsburgh Sleep Quality Index; ESS, Epworth Sleepiness Scale; BDI, Beck Depression Inventory; mm H$_2$O, millimeters of water; d, days.
[a]Control vs OSA before CPAP, P < .05; P values were computed from independent t tests.
[b]OSA pre-CPAP vs post-CPAP, P < .05; P values were computed from dependent t tests.

In this test, "apnea" means that air flow is completely stopped for at least 10 seconds, and "hypopnea" means that air flow is significantly reduced (50% or higher) for at least 10 seconds, or is reduced for at least 10 seconds with stimulation of an electroencephalograph or a decrease in oxygen saturation. All the patients showed very severe OSA (apnea–hypopnea index (AHI)>30), whereas the normal control group showed AHI<5. The clinical diagnosis or history of respiratory diseases, cerebral vascular or coronary arterial heart diseases, endocrine diseases (diabetes, and thyroid diseases), neurological conditions (neurodegenerative diseases, epilepsy, and head injury), mental disorders (recurrent depression, mental abnormality, and material-related disorder), or current intake of psychotropic drugs were excluded from criteria. A cardiologist checked the periodic ECG examination of the participants, and found no significant abnormality.

The results of comparison of the untreated OSA patients with the normal control group indicated that the OSA patients showed the low mean value of SampEn$_{RR}$ (f23.5; P<0.001) and the high mean value of cross-SampeEn (F16.0; P=0.001). In addition, the untreated OSA patients showed high LF and high LF/HF ratio compared to the normal control group.

Figure 9A:
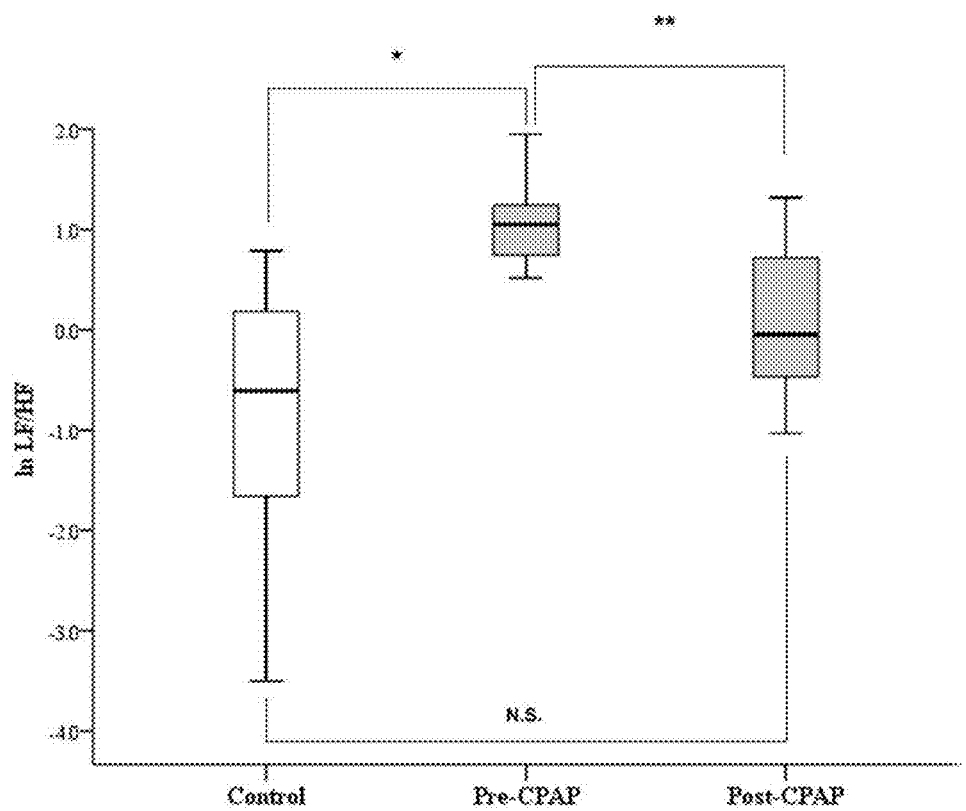
FIGS. 9A and 9B are graphs illustrating the results of measuring the LF/HF ratios and combined cardiac and respiratory indices of OSA patients based on the progress of treatment when the method of assessing treatment effects on obstructive sleep apnea according to an embodiment of the present disclosure is applied.
Figure 9B:
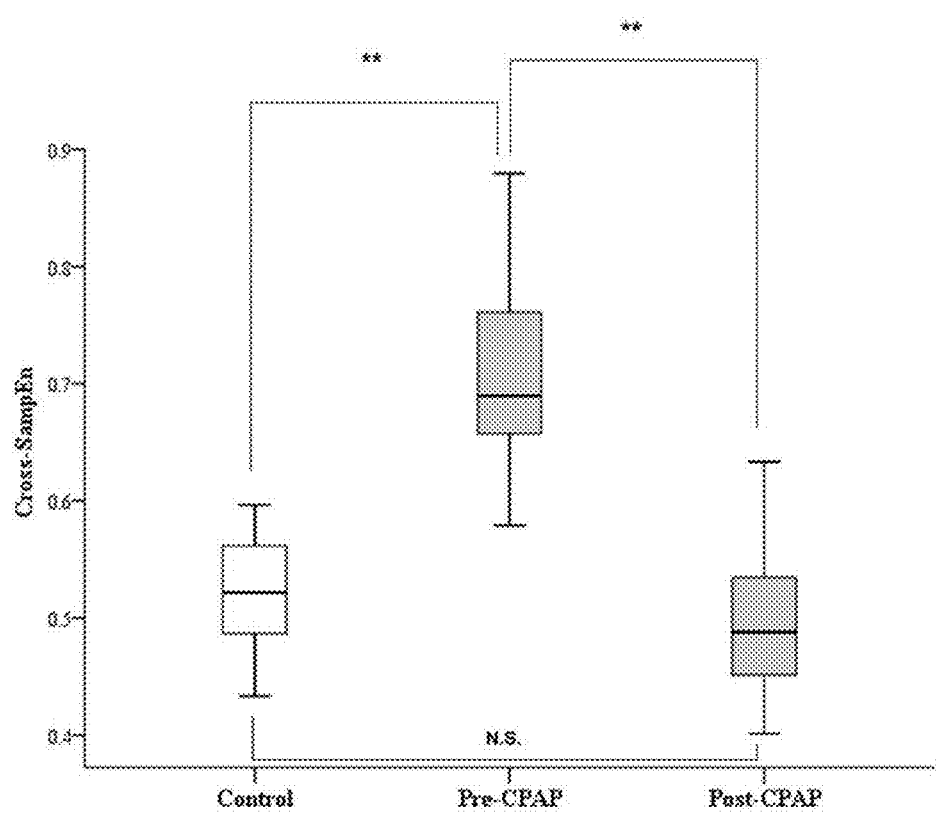

However, as illustrated in FIGS. 9A and 9B, a pair of samples showed a significantly low LF/HF ratio (t-test, 5.2; P<0.001) and a significant increase in SampEnRR (t-test, 4.2; P=0.001) even after CPAP treatment. Furthermore, it can be seen that the samples showed a significant decrease in cross SampEn and an enhanced coupling between the heart rate and the respiration.

In addition, as illustrated in the following Table 2, the mean SampEn value of the CPAP treatment patients with OSA is definitely higher than that of the normal control group, and there is no definite difference in LF/HF ratio and cross-SampEn between the CPAP treatment patients and the normal control group.

TABLE 2

Effects of continuous positive airway pressure treatment on the changes in the autonomic parameters.

| Variable[a] | Pre-CPAP (n = 13) | Post-CPAP (n = 13) | Control (n = 13) | P value[b] | Cohen d[c] | P value[d] |
|---|---|---|---|---|---|---|
| Mean RR | 832.0 (144.2) | 936.2 (132.8) | 892.1 (108.3) | .03 | 0.86 | .72 |
| SD RR | 40.5 (10.7) | 46.3 (14.7) | 53.3 (26.4) | .18 | 0.45 | .79 |
| Mean RI | 3740.5 (126.4) | 3722.0 (88.8) | 3719.1 (101.1) | .69 | 0.03 | .48 |
| SD RI | 100.4 (71.1) | 70.8 (49.7) | 75.6 (63.6) | .07 | 0.48 | .96 |
| RMSSD | 27.0 (10.7) | 34.4 (16.8) | 40.3 (28.4) | .11 | 0.53 | .29 |
| ln LF | 6.4 (0.6) | 5.9 (0.7) | 5.1 (0.8) | .02 | 1.06 | .66 |
| ln HF | 5.4 (0.8) | 5.8 (0.9) | 6.0 (1.2) | .03 | 0.19 | .19 |
| ln LF/HF | 1.0 (0.4) | 0.1 (0.7) | −0.9 (1.4) | <.001 | 0.90 | .12 |
| SampEn$_{RR}$ | 1.32 (0.07) | 1.40 (0.12) | 1.59 (0.11) | .001 | 0.81 | .04 |
| SampEn$_{resp}$ | 0.057 (0.05) | 0.083 (0.06) | 0.034 (0.02) | .20 | 1.10 | .003 |
| Cross-SampEn | 0.71 (0.08) | 0.49 (0.06) | 0.52 (0.05) | <.001 | 0.54 | .04 |

Abbreviations: CPAP, continuous positive airway pressure; Mean RR, mean of all of the beat-to-beat intervals; SD RR, standard deviation of all RR intervals; Mean RI, mean of all of the respiratory iritervals; SD RI, standard deviation of all RIs; RMSSD, mean squared differences of successive RR intervals; LF, low-frequency component of the heart rate power spectrum; HF, high-frequency component of the heart rate power spectrum; SampEn, sample entropy; Cross-SampEn, sample entropy of coupling between beat-to-beat intervals and interbreath intervals.
[a]Data are expressed-as mean (SD).
[b]Comparisons of pre- and post-CPAP values; P values-were computed from a paired-sample t test.
[c]Effect size of CPAP-induced changes in autonomic parameters (0.2-0.4, small; 0.5-0.7, medium; 0.8 or greater, large).
[d]Comparisons of post-CPAP and control Values; P values were computed from an analysis of covariance with BMI as the covariate.

Based on cross-SampEn obtained according to an embodiment of the present disclosure, an abnormality in central autonomic regulation can be quantified, and the response of a patient to CPAP, that is, the standard treatment for OSA, can be also quantified.

As described above, a system for assessing treatment effects on obstructive sleep apnea according to at least one embodiment of the present invention has the advantage of measuring electrocardiograph and respiratory rhythm signals at the same time and then calculating a combined cardiac and respiratory index based on the signals, so that an abnormality in central autonomic regulation can be objectively quantified, and also so that the onset of a cardiovascular disease can be predicted and prevented in advance.

A system for assessing treatment effects on obstructive sleep apnea according to at least one embodiment of the present invention has the advantage of assessing the response of an OSA patient to treatment at low costs using a conventional device for measuring the heart rate variability and respiratory rhythm of the patient, and has the advantage of checking the condition of a patient in a non-invasive manner, so that discomfort is not caused to the patient, and also so that the repulsion of the patient toward the examination of treatment response can be minimized.

A system for assessing treatment effects on obstructive sleep apnea according to at least one embodiment of the present invention has the advantage of assessing the coordination between heart rate and respiratory rhythm based on a combined cardiac and respiratory index.

A system for assessing treatment effects on obstructive sleep apnea according to at least one embodiment of the present invention has the advantage of establishing a treatment method and a plan for each patient based on treatment effects on obstructive sleep apnea and then performing patient-customized treatment, so that the treatment period of obstructive sleep apnea can be reduced, and also so that treatment effects on obstructive sleep apnea can be enhanced.

A system for assessing treatment effects on obstructive sleep apnea according to at least one embodiment of the present invention has the advantage of schematically storing and managing information about the combined cardiac and respiratory index of a normal control group and information about the history of the treatment of obstructive sleep apnea of a patient, so that the objectivity and accuracy of the assessment of the response of the patient to treatment can be ensured.

A system for assessing treatment effects on obstructive sleep apnea according to at least one embodiment of the present invention has the advantage of implementing a bio-signal measurement unit in the form of a portable unit, so that it is possible to measure information about the heart rate variability and respiratory rhythm of a patient at a remote location, to transmit it in real time and thus to monitor the condition of the patient in real time, and also so that the task of assessing the treatment response can be easily performed.

A method for assessing treatment effects on obstructive sleep apnea according to at least one embodiment of the present invention has the advantage of comparing the combined cardiac and respiratory index (obtained by combining heart rate variability and respiratory rhythm signals) of a patient with that of a control group, so that the response of the patient to standard treatment for obstructive sleep apnea can be objectively assessed.

Although the specific embodiments of the present invention have been disclosed for illustrative purposes, those skilled in the art will appreciate that various modifications, additions and substitutions are possible without departing from the scope and spirit of the invention as disclosed in the accompanying claims.

What is claimed is:

1. A method of assessing treatment effects on obstructive sleep apnea, the method comprising:
   (a) measuring each of an electrocardiogram and respiratory rhythm of a patient using a bio-signal measurement unit comprised of an electrocardiogram measurement unit measuring the electrocardiogram and a respiratory rhythm measurement unit which is different from the electrocardiogram measurement unit and measures the respiratory rhythm;
   (b) obtaining, with a combined index calculation unit comprised of a heart rate variability entropy calculation unit, a respiratory rhythm entropy calculation unit, and a cross-sample entropy calculation unit, a combined cardiac and respiratory index by combining heart rate variability and respiratory rhythm signals, measured at the step (a), the obtaining comprises:
   (b-1) calculating heart rate variability sample entropy ($SampEn_{RR}$) using the heart rate variability entropy calculation unit, and calculating respiratory rhythm sample entropy ($SampEn_{rep}$) using the respiratory rhythm entropy calculation unit; and
   (b-2) obtaining the combined cardiac and respiratory index (Cross-SampEn) by combining the heart rate variability sample entropy with the respiratory rhythm sample entropy using the cross-sample entropy calculation unit;
   (c) assessing, with a treatment response assessment unit, a response of the patient to treatment of obstructive sleep apnea by using the combined cardiac and respiratory index,
   wherein an abnormality in central autonomic regulation is quantified and a response of a patient to continuous positive airway pressure (CPAP) is quantified based on the combined cardiac and respiratory index,
   wherein the step (c) comprises:
   assessing the treatment effects on obstructive sleep apnea based on a change in the combined cardiac and respiratory index or a difference of the combined cardiac and respiratory index from that of a normal control; and
   determining that the coordination between heart rate and respiratory rhythm is low if a value of the combined cardiac and respiratory index is higher than an upper limit of a normal range, and determining that the coordination between heart rate and respiratory rhythm is high if the value of the combined cardiac and respiratory index is lower than a lower limit of the normal range,
   wherein the heart rate variability sample entropy and the respiratory rhythm sample entropy at the step (b) are calculated using density correlation functions $C_{i,m}(r)$ $C_{i,(m+1)}(r)$:

$$SampEn(m, r, N) = -ln(c_{(m+1)}(r)/c_m(r))$$

$$C_{i,m}(r) = \frac{n_{i,m}(r)}{N - m + 1}$$

$$C_{i,(m+1)}(r) = \frac{n_{i(m+1)}(r)}{N - m - 1}$$

wherein for given a time series of x(i)=1, 2, 3, K, N, m and r are input parameters, m is the size of a regeneration vector of a phase, r is a filtering level, $n_{i,m}(r)$ and $n_{i,(m+1)}(r)$ are the numbers of vectors similar to a respective vector, $C_m(r)$ and $C_{(m+1)}(r)$ that are averages of $C_{i,m}(r)$ and $C_{i,(m+1)}(r)$ respectively are calculated for i=1, 2, K, N−m.

2. The method of claim 1, wherein the normal range of the combined cardiac and respiratory index is a range from 0.46 to 0.58.

3. The method of claim 1, further comprising, after the step (c), establishing a treatment method and a plan for the patient based on treatment effects on obstructive sleep apnea using a customized management unit.

4. The method of claim 3, further comprising, after the step (c), storing and managing information about the combined cardiac and respiratory index of the normal control and information about a history of treatment of obstructive sleep apnea of the patient using a treatment/assessment information unit.

5. The method of claim 1, wherein the bio-signal measurement unit is implemented in a portable form that can be carried by the patient, and is attached to or worn on a wrist and chest of the patient and measures the electrocardiogram and respiratory rhythm of the patient; and further comprises a separate data communication unit, and transmits the measured electrocardiogram and respiratory rhythm to an external location.

6. The method of claim 5, wherein the bio-signal measurement unit and the separate data communication unit are included in a smartphone.

7. A method of assessing treatment effects on obstructive sleep apnea, the method comprising:
  (a) measuring an electrocardiogram of a patient by using an electrocardiogram measurement unit worn on a wrist of the patient and measuring respiratory rhythm of the patient by using a respiratory rhythm measurement unit which is worn on a chest of the patient, wherein an electrocardiogram measurement unit and the respiratory rhythm measurement unit area each in a portable form;
  (b) obtaining, with a combined index calculation unit comprised of a heart rate variability entropy calculation unit, a respiratory rhythm entropy calculation unit, and a cross-sample entropy calculation unit, a combined cardiac and respiratory index by combining heart rate variability and respiratory rhythm signals, measured at the step (a), the obtaining comprises:
    (b-1) calculating heart rate variability sample entropy ($SampEn_{RR}$) using the heart rate variability entropy calculation unit, and calculating respiratory rhythm sample entropy ($SampEn_{rep}$) using the respiratory rhythm entropy calculation unit; and
    (b-2) obtaining the combined cardiac and respiratory index (Cross-SampEn) by combining the heart rate variability sample entropy with the respiratory rhythm sample entropy using the cross-sample entropy calculation unit;
  (c) assessing, with a treatment response assessment unit, a response of the patient to treatment of obstructive sleep apnea by using the combined cardiac and respiratory index,
  wherein an abnormality in central autonomic regulation is quantified and a response of a patient to continuous positive airway pressure (CPAP) is quantified based on the combined cardiac and respiratory index,
  wherein the step (c) comprises:
    assessing the treatment effects on obstructive sleep apnea based on a change in the combined cardiac and respiratory index or a difference of the combined cardiac and respiratory index from that of a normal control; and
    determining that the coordination between heart rate and respiratory rhythm is low if a value of the combined cardiac and respiratory index is higher than an upper limit of a normal range, and determining that the coordination between heart rate and respiratory rhythm is high if the value of the combined cardiac and respiratory index is lower than a lower limit of the normal range,
  wherein the heart rate variability sample entropy and the respiratory rhythm sample entropy at the step (b) are calculated using density correlation functions $C_{i,m}(r)$ and $C_{i,(m+1)}(r)$:

$$SampEn(m, r, N) = -ln(c_{(m+1)}(r)/c_m(r))$$

$$C_{i,m}(r) = \frac{n_{i,m}(r)}{N-m+1}$$

$$C_{i,(m+1)}(r) = \frac{n_{i(m+1)}(r)}{N-m-1}$$

wherein for given a time series of x(i)=1, 2, 3, K, N, m and r are input parameters, m is the size of a regeneration vector of a phase, r is a filtering level, $n_{i,m}(r)$ and $n_{i,(m+1)}(r)$ are the numbers of vectors similar to a respective vector, $C_m(r)$ and $C_{(m+1)}(r)$ that are averages of $C_{i,m}(r)$ and $C_{i,(m+1)}(r)$ respectively are calculated for i=1, 2, K, N−m.

* * * * *